Nov. 23, 1954 F. W. ANDERSON Plant Pat. 1,324

NECTARINE TREE

Filed March 29, 1954

WITNESS

Addison J. Avery

INVENTOR

Frederic W. Anderson

Webster & Webster

ATTYS.

United States Patent Office

Plant Pat. 1,324

Patented Nov. 23, 1954

1,324

NECTARINE TREE

Frederic W. Anderson, Merced, Calif.

Application March 29, 1954, Serial No. 419,630

1 Claim. (Cl. 47—62)

The present invention is directed to a new and distinct variety of nectarine tree; the primary object of the invention having been to provide a nectarine tree which bears fruit having commercially desirable characteristics.

The novelty of the present variety of nectarine tree resides primarily in the ripening period, and the size, color, flesh, texture, and keeping and shipping qualities of the fruit.

In particular the fruit of the herein claimed variety of nectarine tree ripens about two weeks after the Freedom nectarine (United States Plant Patent No. 1161), or substantially with the Stanwick nectarine (unpatented), which latter has long been a standard shipping variety in the State of California. Although ripening with the Stanwick nectarine, the fruit of the present variety is superior for commercial shipping and market use, as the freestone fruit is yellow fleshed instead of white, larger by approximately 50%, firmer in texture, has more external red color, and is of a quality which keeps and ships better, especially for long distance shipping.

The present new and distinct variety of nectarine was originated by me in my experimental nursery and orchard near Merced, California, as part of a long and continuing nectarine breeding project; the purpose of such project having been the origination and development of superior nectarines for commercial use.

The instant variety is one of a number of seedlings produced from seeds of the clingstone nectarine Le Grand (United States Plant Patent No. 549); the pistils of whose flowers were artificially pollinated by me from flowers of an unnamed yellow fleshed nectarine that had resulted from a cross (F–1) between Le Grand and Kim (United States Plant Patent No. 173) nectarines.

All of the foregoing seedlings were yellow fleshed, but had distinguishable variations in size, shape, period of ripening, and other characteristics.

By careful and continuing observation I determined that one of such seedlings, which is the instant variety, had superior characteristics for commercial planting, and market use of the fruit, relative to any freestone nectarine ripening at the same time; i. e., substantially with the Stanwick nectarine, as aforesaid.

Subsequent to my origination and selection of the present variety I have successfully top-worked it on orchard trees in my experimental nursery, as aforesaid, and these asexual reproductions have been found to run true in all respects.

Figure 1:
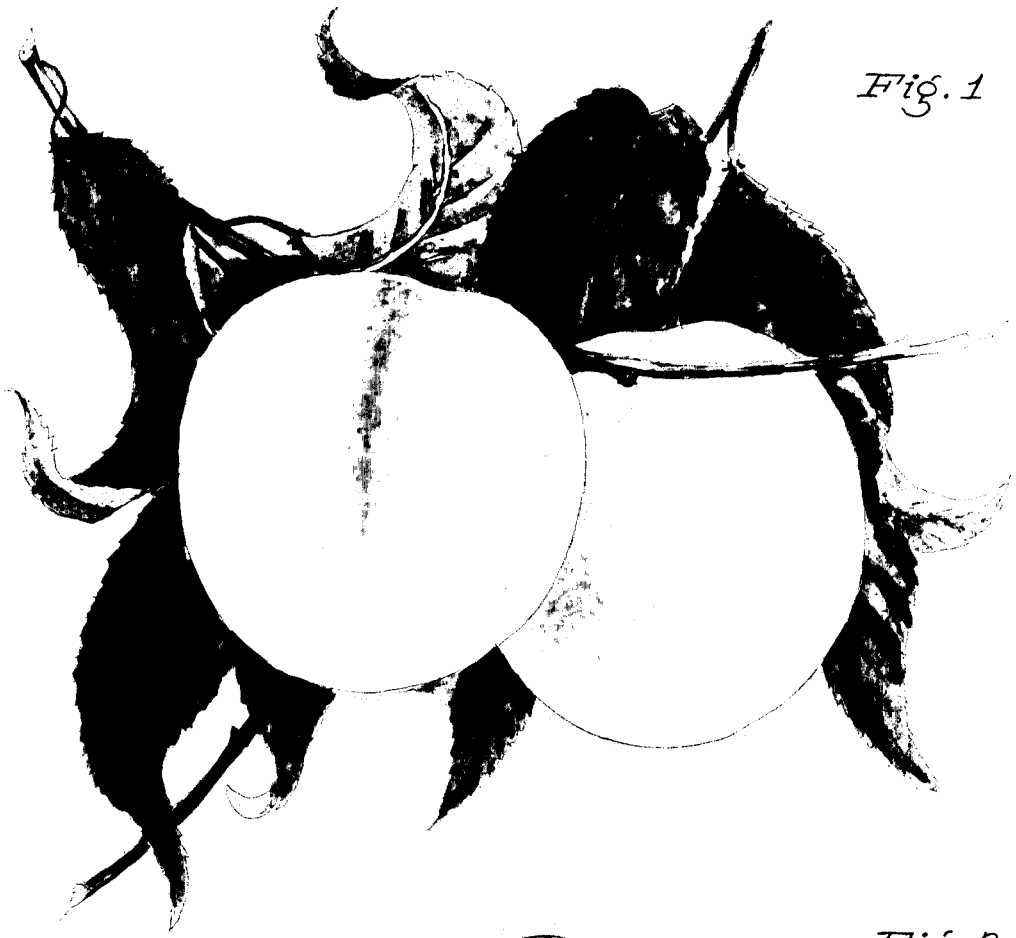
Fig. 1 is an elevation showing two of the fruit of the present variety, together with twigs and leaves.
Figure 2:
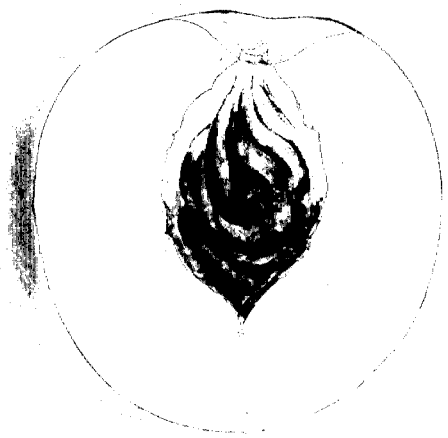
Fig. 2 is a sectional elevation of one of the fruit with the stone exposed.
Figure 3:
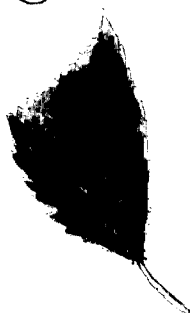
Fig. 3 is a fragmentary elevation of one of the leaves.

Referring now more specifically to the pomological details of this new and distinct variety of nectarine tree, the following is an outline description thereof; all major color plate identifications being by reference to Maerz and Paul Dictionary of Color:

Tree: Medium to large; vigorous; spreading; open; vase formed; hardy; productive; regular bearer.

Trunk: Medium to stocky. Medium texture.

Branches: Medium length. Medium thickness. Medium texture. Color—grey. Lenticels—medium number; medium size.

Leaves: Rather large. Average length—6½". Average width—1¾". Acutely pointed. Medium thickness. Smooth.

*Color.*—Top side—medium green (23–L–7). Under side—lighter green (22–K–3).

*Margin.*—Glandular; crenate.

*Pistil.*—About average or medium in length and thickness.

*Glands.*—Average two or three on petiole. Some on basal portion of the blade. Alternate; large; reniform. No stipules.

Flower buds: Medium to large. Medium length. Conic.

Flowers: Dates of first and full bloom are about with the Elberta peach (unpatented). Medium blooming period compared with other varieties. Large showy type with red anthers producing viable pollen. Color—pink.

Fruit:

*Maturity when described.*—Eating ripe.

*Date of first picking.*—August 20, 1953.

*Date of last picking.*—August 28, 1953.

*Size.*—Uniform to variable. Very large, averaging over 3" in axial diameter, and 2¾" transversely in the suture plane. In many well grown specimens the fruit averages 3" in all diameters.

*Form.*—Globuse to slightly oblong.

*Suture.*—Distinct but shallow, extending from base to beyond the pistil point; there being a marked depression beyond said pistil point.

*Ventral surface.*—Rounded, with equal lips.

*Cavity.*—Abrupt; circular. Elongated in suture plane with suture showing on one side. Average depth—⅜". Average breadth—⅝". Markings—none.

*Base.*—Rounded.

*Apex.*—Short; mamiform. Depressed, with very short pistil point.

*Stem.*—Heavy and adheres closely to stone, so that fruit hangs well on the tree when ripe.

Skin: Thin to average thickness. Tough to medium. Adheres tenaciously to flesh.

*Down.*—Wanting.

*Color.*—Yellow (9–L–5 shading to 9–L–8), mottled over a substantial portion with orange red (1–F–12), shading to a deeper red (3–L–6), overlaid in part with red streaks (6–L–6).

Flesh:

*Amygdalin.*—Moderate.

*Juice.*—Moderate.

*Texture.*—Firm; meaty.

*Fibers.*—Coarse.

*Ripens.*—Even.

*Flavor.*—Sub-acid; mild.

*Aroma.*—Not very pronounced.

*Eating quality.*—Fair to good.

*Color.*—Yellow (9–L–6), with faint reddish markings (1–G–9) throughout, mottled with red (1–K–9) next to stone.

Stone: Free. Parts from flesh smoothly.

*Size.* — Large. Average length — 1½". Average breadth—1¼". Average thickness—⅞".

*Form.*—Oblong to oval.

*Base.*—Oblique.

*Hilum.*—Oval.

*Apex.*—Acute.

*Sides.*—Unequal.

*Surface.*—Irregularly furrowed and pitted throughout.

*Ridges.*—Jagged.

*Pits.*—Elongated.

*Ventral edge.*—Thin.

*Dorsal edge.*—Full, with broad groove.

*Ridges.*—Continuous.

*Tendency to split.*—Moderate.

*Color.*—Brown (7–L–4) shading to a reddish pink (2–J–7) adjacent the base end.

Use: Market; shipping.

Keeping quality: Good.

Shipping quality: Good.

Resistance to disease: No unusual susceptibility noted, and the usual spray practices have maintained under control those insects and diseases that are prevalent in the orchard areas of California.

The tree and its fruit herein described may vary in slight detail due to climatic and soil conditions under which the variety may be grown.

Having thus described my invention, I claim:

A new and distinct variety of nectarine tree, as described and illustrated, characterized—as compared with the Stanwick nectarine—by freestone fruit which is yellow instead of white fleshed, approximately 50% larger in size, with more exterior red color, of better keeping and shipping qualities, and having substantially the same ripening period, which period is approximately two weeks later than the Freedom nectarine; and further characterized by fruit having strong stems, which fruit hangs well on the tree when ripe.

No references cited.